United States Patent [19]

Gemelke

[11] 4,252,127
[45] Feb. 24, 1981

[54] PORTABLE BLOOD PRESSURE RECORDER

[75] Inventor: Ronnie L. Gemelke, Ames, Iowa

[73] Assignee: Iowa State University Research Foundation, Ames, Iowa

[21] Appl. No.: 50,135

[22] Filed: Jun. 19, 1979

[51] Int. Cl.³ .............................................. A61B 5/02
[52] U.S. Cl. .................................. 128/680; 128/683; 128/900; 346/33 ME
[58] Field of Search .............................. 128/679–683, 128/710, 900; 346/33 ME

[56] References Cited

U.S. PATENT DOCUMENTS

| | | | |
|---|---|---|---|
| 3,085,567 | 4/1963 | Vigilante | 128/683 |
| 3,905,354 | 9/1975 | Lichowsky | 128/681 |
| 4,033,336 | 7/1977 | Murawski et al. | 346/33 ME |

FOREIGN PATENT DOCUMENTS 2811362  11/1978  Fed. Rep. of Germany ........... 128/681

OTHER PUBLICATIONS

Schneider, R. A. et al., "A Fully Automatic Portable BP Recorder", Jrnl. for Adv. of Med. Instr. Mar–Apr. 1972, vol. 6 #2 p. 189.

*Primary Examiner*—Kyle L. Howell
*Assistant Examiner*—Francis J. Jaworski
*Attorney, Agent, or Firm*—Tilton, Fallon, Lungmus & Chestnut

[57] ABSTRACT

A portable blood pressure recorder device for an ambulatory subject having an inflatable occluding cuff, a pump for inflating the cuff, a sensor for detecting Korotkoff sounds, a transducer for detecting pressure in the cuff, a variable voltage reference and signal circuitry system for encoding a pressure signal from the transducer into pressure segments, a recording system for combining the Korotkoff sounds with the encoded pressure segments, circuitry for activating and deactivating components of the device, and a data retrieval system for interpreting recorded data.

7 Claims, 1 Drawing Figure

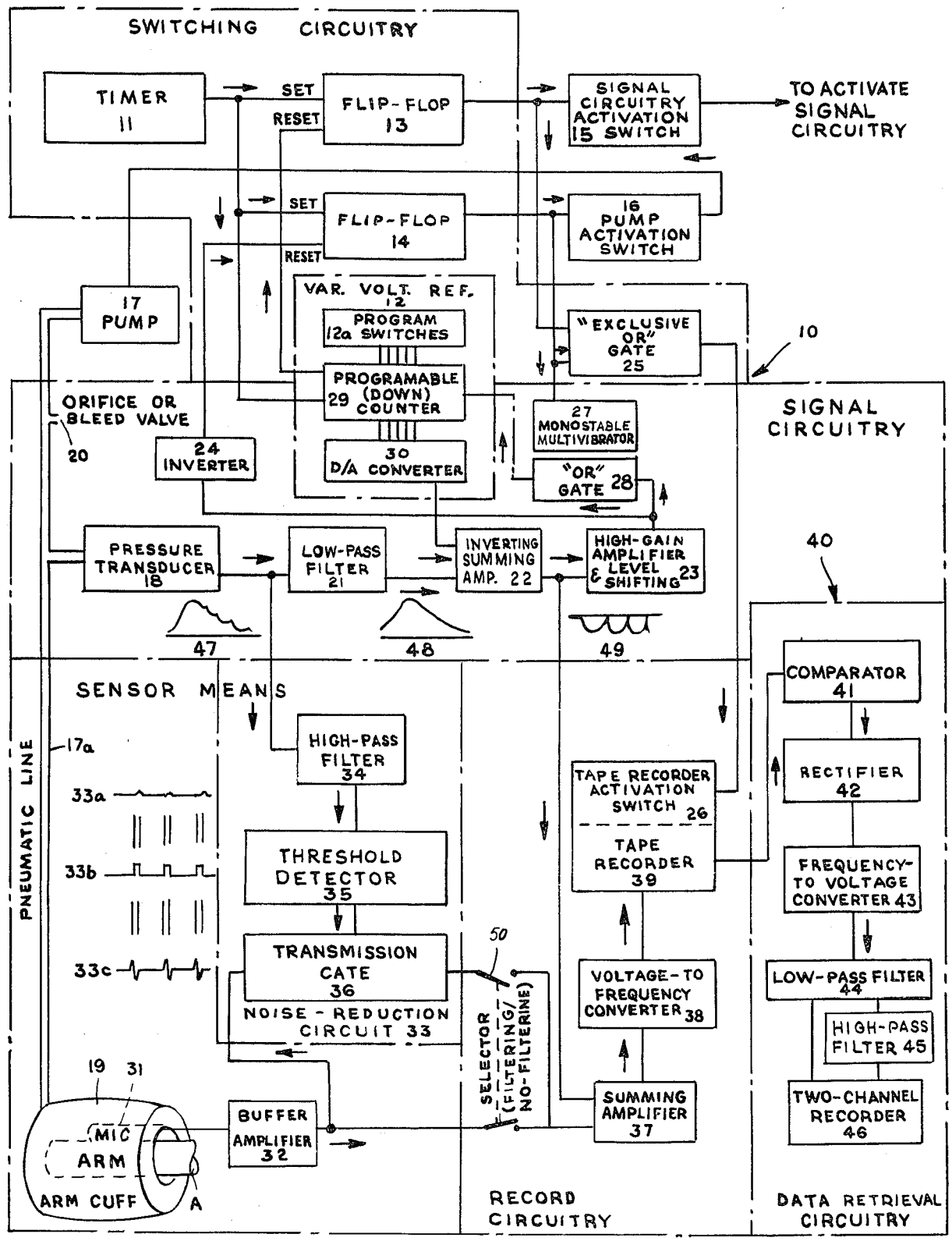

PORTABLE BLOOD PRESSURE RECORDER

BACKGROUND AND SUMMARY OF THE INVENTION

This invention relates to a blood pressure recorder, and more particularly, to a portable blood pressure recorder for an ambulatory subject. Blood pressure measurement is valuable in clinical medicine and experimental psychology, and is performed by direct and indirect methods. When systolic and diastolic pressures are sufficient, an indirect method is normally employed thereby avoiding the trauma and possibilities of infection associated with the direct method.

Nearly all indirect methods occlude the blood vessel through application of counterpressure on the body surface. Certain physiological events are detected as this counterpressure is varied. Systolic and diastolic pressures are equated to this counterpressure whenever specific changes in these physiological events occur.

The following references are generally representative of the present art:
U.S. Pats.
  Nakayama et al: No. 4,144,879
  Matsuoka et al: No. 4,105,020
  Kaspari et al: No. 4,058,117
  Yen et al: No. 3,978,848
  Lichowsky: No. 3,905,353
  Lickowsky: No. 3,905,354
Publication of Del Mar Avionics dated 12/77 ("Ambulatory Pressurometer II System")

Available instruments for blood pressure determination are less than ideal for several reasons. Application is generally restricted to specific subject activities and locations, the subject normally being seated or recumbent, and in a fixed setting, such as a doctor's office or a nursing station. Most instruments are manually operated, requiring supervision and thereby limiting the amount of data which can be generated practically. Furthermore, many blood pressure instruments provide questionable measurements due to noise-related data reduction. Noise is typically detected at the same frequency and amplitude as the signal. Data reduction in the early stages of measurement reduces the capability of subsequently sorting out a signal from remaining noise. In addition, blood pressure may be significantly affected by the subject's emotional response to the process of blood pressure measurement. These restrictions are especially severe when the application involves numerous indirect measurements on ambulatory subjects.

The invention overcomes these limitations by providing a portable device which allows relatively unrestricted movement of the ambulatory subject, automatically measures blood pressure periodically throughout eight or more hours of a day, and stores this information for later retrieval and analysis. The invention utilizes the auscultatory method to measure blood pressure. A standard inflatable occluding cuff is wrapped around a subject's arm for measurement purposes. A microphone, taped securely at the antecubital fossa (brachial artery) and compressed by the arm cuff, detects Korotkoff sounds. When the device is activated, a pump pressurizes the cuff. Once a predetermined pressurized level is reached in the cuff, the pump is deactivated and measurement begins. The pressure in the cuff falls until a lower setting is reached. As the pressure decreases, data is collected in encoded, uniform pressure segments. The data is then recorded for subsequent analysis.

DETAILED DESCRIPTION

The drawing is a block diagram of the switching and recording circuitry.

A blood pressure recording device 10 is generally shown in block diagram form in the drawing. A measurement cycle is initiated by a high signal of 3 milliseconds duration produced at the manual switch or timer 11. The high signal presets the variable voltage reference 12 to a desired negative level, as will be discussed later. The high signal also sets flip-flops 13 and 14 which activate the signal circuitry switch 15 and pump switch 16, respectively.

Pump switch 16, once activated, supplies power to pump 17, allowing the pressure cycle to begin. The pump 17 supplies pressurized air to a solid state pressure transducer 18 and to an arm cuff 19 wrapped around a subject's arm A. A finger or leg cuff may be used in place of the arm cuff. An orifice or bleed valve 20 is provided between the pump and cuff for an exponential pressure deflation rate. In the preferred embodiment, the valve has an opening created by a twenty-two gauge hypodermic needle. The loss of air through the valve guarantees cuff deflation when pump 17 is deactivated.

Cuff inflation rate is dependent on both the pump rate and the orifice size, whereas the deflation rate is dependent only on orifice size. Inflation of a standard adult cuff to 160 mm Hg pressure requires thirty seconds when operating with a twenty-two gauge needle and a fifteen volt pump supply. If a higher pressure is desired, a greater length of time is needed. The deflation rate of the standard adult cuff, using the twenty-two gauge needle, is approximately six mm Hg per second. Other rates may be conveniently selected by substitution of other gauge needles. A faster inflation rate accompanies a slower deflation rate when a smaller orifice is used. Although the pressure drop is not linear, this should not be detrimental, because the slower rate at lower pressure allows for higher accuracy for diastolic pressures.

As the cuff pressure rises, pressure transducer 18 produces a voltage signal proportional to this pressure. The voltage signal is then fed into low-pass RC filter 21 to remove alternating pressure variation (pneumatic noise) corresponding to several mm Hg pressures, produced by each movement of the pump's diaphragm (not shown). The filtered positive signal is then added to the present negative reference voltage at inverting summing amplifier 22. When the cuff pressure exceeds the reference, amplifier 22 output goes negative and high-gain amplifier and level-shifter 23 amplifies the signal and converts the signal to be compatible with C-MOS circuitry. Thereafter, inverter 24 creates a resulting high signal which resets flip-flop 14. The output of flip-flop 14 goes low, thereby deactivating the pump and allowing cuff pressure to begin falling.

Recording circuitry is activated when the cuff pressure begins to fall. The resetting of flip-flop 14, as mentioned above, permits exclusive-OR gate 25 to have a high output signal and activate the tape recorder switch 26. The setting of flip-flop 14 also initiates a positive pulse of 2 milliseconds duration from monostable multivibrator 27. The pulse causes a high pulse output from OR gate 28 and consequently a high clock input to the down counter 29 of the variable voltage reference 12. The counter 29 then counts down by one, thereby causing the output from digital/analog (D/A) converter 30 to decrease by a value representing 10 mm Hg. When this occurs, the pressure transducer 18 output voltage is higher than the magnitude of the D/A converter output voltage, and will continue to be so, except for the brief periods of variable voltage reference pressure switching. The cuff continues to deflate. When the pressure transducer output reaches the magnitude of the new voltage reference level, summing amplifier 22 output goes positive causing the OR gate 28 to have a high pulse output and making the down counter 29 again count down one. The output from the D/A converter 30 is again reset 10 mm Hg lower. This process continues until the counter 29 reaches zero. The pressure waveform is encoded into 10 mm Hg pressure segments for two purposes. One purpose is to provide the desired pressure signal for the record circuitry to process. The other purpose is to activate and deactivate power supplies (not shown) at the proper pressure levels.

When the counter has reached zero, D/A converter 30 has a voltage output corresponding to 30 mm Hg pressure. The down counter then sends a positive pulse to reset flip-flop 13 thereby deactivating the signal circuitry and the tape recorder. The system is reactivated when the next pressure cycle is initiated by timer 11.

A small crystal microphone 31, taped securely at the antecubital fossa (not shown) and compressed by the arm cuff 19, acts as a sensor to detect Korotkoff sounds. Other types of sensors may be used. The microphone requires an amplifier input impedance of over one megohm, which is achieved by passing the signal from the microphone through buffer amplifier 32.

The output signal from buffer amplifier 32 may either be directly recorded or pass through the noise-reduction circuit 33 before recording. The noise-reduction circuit 33 prevents the recording of much of the noise occurring between heartbeats in the following manner.

Each heartbeat causes a slight increase in pressure in the arm cuff 19. This pressure increase shows up as an increase in the pressure transducer's output. Noise-reduction begins by feeding the signal through high-pass filter 34 in order to eliminate the dc pressure signal. The occurrence of each heartbeat induced pressure pulse is subsequently identified in threshold detector 35. Transmission gate 36 or another suitable circuit allows microphone signals to reach summing amplifier 37 only if the heartbeat signal from the threshold detector 35 is present. A switching section 50 allows selection of either the filtered microphone signal, created above, or the unfiltered signal from buffer amplifier 32 to reach summing amplifier 37.

Summing amplifier 37 adds the microphone signal to the voltage encoded pressure signal and scales the result to one volt for the pressure signal and one volt for the Korotkoff sound signal. The composite signal is then frequency modulated by voltage-to-frequency converter 38. The output, a waveform with a constant off-time occurring at a variable frequency, is subsequently recorded by portable tape recorder 39.

Data stored in the tape recorder 39 can be sent to data retrieval circuitry, generally designated as numeral 40. The signal from the tape recorder 39 is passed through comparator 41 and then rectifier 42. Thereafter it is fed into a frequency-to-voltage converter 43. The signal is then passed through a filter where it is subject to low-pass filter 44 and high-pass filter 45. Low-pass filtering eliminates undesirably high frequencies. High-pass filtering eliminates the pressure ramp of the encoded pressure signal and undesirable low-frequencies of the Korotkoff sounds. Besides including Korotkoff sounds, this second signal includes 10 mm Hg pressure markers which pass through the filter.

Interpretation of the recorded data is most easily accomplished by reading the Korotkoff sounds from the high-pass filtered recording and reading the pressure from the composite recording. For this reason, the signal preceding and the signal following the high-pass filter 45 are recorded side-by-side on a two-channel strip-chart recorder 46. The high-pass filtered signal displays the sounds most distinctly and also allows for selection of a specific frequency range.

It will be appreciated that a variety of equipment may be employed in the practice of the invention. For example, the pump means illustrated here as the pump activation switch 16, pump 17, pneumatic line 17a, and bleed valve 20 may take other forms for inflating the occluding cuff 19.

Korotkoff sounds are detected by a sensor means which here includes the microphone 31, buffer amplifier 32, and the noise reduction circuit 33. The noise reduction circuit 33 itself may be broken up into three functional components. High pass filter 34 eliminates the direct current signal from the output signal of the pressure transducer. Output from the high pass filter is represented by waveform 33a. A threshold detector 35 then acts as a means for identifying heart beat induced pressure pulses from the pressure signal. Output from threshold detector 35 is represented by waveform 33b. This signal and the signal from buffer amplifier 32 are fed into transmission gate 36 which permits an output signal only when the heart beat is present. This signal as represented by waveform 33c is subsequently combined with encoded pressure signal segments and recorded for subsequent analysis.

Pressure transducer 18 and low pass RC filter 21 constitute transducer means for detecting pressure in the occluding cuff. Waveform 47 represents the initial output signal from pressure transducer 18. This signal is subsequently smoothed by low pass RC filter 21 as represented by waveform 48.

Program switches 12, counter 29, and digital-to-analog converter 30 constitute variable voltage reference means for encoding at amplifier 22 a pressure signal from the transducer means into pressure segments having upper and lower level limits. The size of the pressure segments and the upper and lower level limits for pressure are preset by program switches 12. Each segment is associated with a particular value in down counter 29. Digital-to-analog converter 30 transforms this value from a digital number into an analog signal which is then added to waveform 48.

Selector 50, summing amplifier 37, voltage-to-frequency converter 38, tape recorder activation switch 26, and tape recorder 39 make up the elements of the recording means for combining Korotkoff sounds with the encoded pressure signal and processing the combined signal.

Timer 11, flip-flops 13 and 14, and Exclusive-OR gate 25 comprise the switching circuitry means for presetting the variable voltage reference and for activating and deactivating the signal means, the pumping means, and the recording means.

Summing amplifier 22, high gain amplifier and level shifter 23, OR gate 28, monostable multivibrator 27, and inverter 24 constitute signal circuitry means for comparing and summing the signal from the transducer means and the signal from the variable voltage reference means to develop encoded pressure segments. The signal from digital-to-analog converter 30 represents a particular pressure segment. This negative signal is added to waveform 48 at summing amplifier 22. The output of summing amplifier 22 is subsequently combined with Korotkoff sounds and recorded for later analysis. The level of the variable voltage reference means is reset for the next lower pressure segment when the output of the transducer means exceeds the upper limit level. The signal from the variable voltage reference means is reset each time the output of the transducer means reaches the new reset level until the lowest level is reached thereby deactivating the signal circuitry means and recording means.

Comparator 41, rectifier 42, frequency to voltage converter 43, filters 44 and 45 and two-channel recorder 46 constitute the decoder data retrieval means whereby recorded data may be interpreted.

While in the foregoing specification, a detailed description of an embodiment of the invention has been set down for the purpose of illustration, variations in the details hereingiven may be made by those skilled in the art without departing from the spirit and scope of the invention.

What I claim is:

1. A portable blood pressure recorder device for an ambulatory subject comprising:
    an inflatable occluding cuff;
    pump means for inflating said cuff;
    sensor means for detecting Korotkoff sounds in an artery occluded by said cuff;
    transducer means for detecting pressure in said cuff;
    variable voltage reference means for encoding a pressure signal from said transducer means into pressure segments having upper and lower level limits;
    recording means for combining said Korotkoff sounds with said encoded pressure signal and processing the combined signal;
    switching circuitry means for setting the initial level of said variable voltage reference means and for activating and deactivating the signal means, the pumping means, and the recording means;
    signal circuitry means for comparing and summing the said signal from the transducer means and the signal from the variable voltage reference means to develop encoded pressure segments, said level of the variable voltage reference means being reset for the next lower pressure segment when the output of the transducer means exceeds the magnitude of the upper limit level and said level being subsequently reset to the next lower segment each time the output of the transducer means reaches the magnitude of said level until the lowest level is reached thereby deactivating the signal circuitry means and recording means;
    and decoder data retrieval means interconnected to said recording means for interpreting recorded data.

2. The device of claim 1 wherein said pump means includes a small orifice for pressure deflation.

3. The device of claim 1 wherein said sensor means includes a crystal microphone, a buffer amplifier, and noise-reduction means for reducing noise occurring between measured heartbeats.

4. The device of claim 3 wherein said noise-reduction means includes filtering means for eliminating direct current pressure signal from the output signal of said pressure transducer, means for identifying heartbeat induced pressure pulses, and means for transmitting a signal only when the heartbeat pulse is present.

5. The device of claim 1 wherein said variable voltage reference includes means for setting upper and lower level limits for said pressure segments, means for changing levels, and means for converting a digital signal to an analog signal.

6. The device of claim 1 wherein said recording means includes a summing amplifier, a voltage-to-frequency converter, and a tape recorder.

7. The device of claim 1 wherein said decoder data retrieval means includes comparator means, rectifying means, a frequency-to-voltage converter, filtering means for said recorded data, and a two-channel recorder.

* * * * *